US009931236B2

(12) United States Patent
Williamson et al.

(10) Patent No.: US 9,931,236 B2
(45) Date of Patent: Apr. 3, 2018

(54) PHYSIOTHERAPEUTIC, AMBULATORY, AND MOBILITY VEST

(71) Applicant: AbiliLife, Inc., Pittsburgh, PA (US)

(72) Inventors: Courtney Williamson, Pittsburgh, PA (US); Keith Joseph, Windermere, FL (US); Liana Kong, Vandalia, OH (US); Amber Ohiokpehai, Lutherville, MD (US)

(73) Assignee: Abililife, Inc., Pittsburgh, PA (US)

( * ) Notice: Subject to any disclaimer, the term of this patent is extended or adjusted under 35 U.S.C. 154(b) by 373 days.

(21) Appl. No.: 14/728,138

(22) Filed: Jun. 2, 2015

(65) Prior Publication Data
US 2016/0074201 A1 Mar. 17, 2016

Related U.S. Application Data

(60) Provisional application No. 62/049,671, filed on Sep. 12, 2014.

(51) Int. Cl.
A61F 5/00 (2006.01)
A61F 5/02 (2006.01)

(52) U.S. Cl.
CPC .............. A61F 5/026 (2013.01); A61F 5/028 (2013.01)

(58) Field of Classification Search
CPC .................................... A61F 5/06; A41B 1/08
(Continued)

(56) References Cited

U.S. PATENT DOCUMENTS 1,417,250 A 5/1922 Kelly
3,029,810 A 4/1962 Martin
(Continued)

FOREIGN PATENT DOCUMENTS

WO 2013138214 9/2013
WO 2013138468 9/2013
WO 2013156394 10/2013

OTHER PUBLICATIONS

Bloem, B.R. et al., "Prospective Assessment of Falls in Parkinson's Disease", J. Neurol, 2001, 950-958, vol. 248, Steinkopff Verlag 2001.

(Continued)

Primary Examiner — Kim M Lewis
(74) Attorney, Agent, or Firm — Buchanan Ingersoll & Rooney PC

(57) ABSTRACT

A physiotherapeutic device has a waist tensioning system and a spine support system that enable correction and/or maintaining postural stance for individuals suffering from poor posture and/or neurodegenerative disease. The device provides a posture support and retention system during episodes of postural instability to enable individuals to maintain posture and balance while performing functions. The device includes a garment with shoulder straps extending from the tensioning system to generate force vectors in a direction opposite of those generated by traditional shoulder straps. A rigid support member is disposed in the garment to run parallel with the spinal column. The shoulder straps and waist straps tie into an anchor located on a portion of the garment directly over the support member. The connected components work in concert to actively and passively adjust tension and apply pressure to straighten shoulders and improve the upper back support.

20 Claims, 7 Drawing Sheets

(58) Field of Classification Search
USPC .................................... 2/69, 44, 45; 602/19
See application file for complete search history.

(56) References Cited

U.S. PATENT DOCUMENTS

| | | | |
|---|---|---|---|
| 3,282,264 A * | 11/1966 | Connelly | ............. A61F 5/026 |
| | | | 450/96 |
| 3,351,053 A | 11/1967 | Stuttle | |
| 3,871,367 A | 3/1975 | Miller | |
| 3,927,665 A | 12/1975 | Wax | |
| 4,202,327 A | 5/1980 | Glancy | |
| 4,688,558 A | 8/1987 | Hooper, Jr. et al. | |
| 4,833,730 A | 5/1989 | Nelson | |
| 5,067,484 A | 11/1991 | Hiemstra-Paez | |
| 5,451,200 A | 9/1995 | LaBella et al. | |
| 5,599,286 A | 2/1997 | Labelle et al. | |
| 5,599,287 A | 2/1997 | Beczak, Sr. et al. | |
| 5,833,638 A | 11/1998 | Nelson | |
| 5,957,873 A | 9/1999 | Allen | |
| 6,063,046 A | 5/2000 | Allum | |
| 6,068,606 A | 5/2000 | Castel et al. | |
| 6,102,879 A | 8/2000 | Christensen et al. | |
| 6,676,617 B1 | 1/2004 | Miller | |
| 7,654,972 B2 | 2/2010 | Alleyne | |
| 7,662,121 B2 | 2/2010 | Zours | |
| 7,785,282 B2 | 8/2010 | Rauch | |
| 7,837,639 B2 | 11/2010 | Jinright et al. | |
| 8,007,457 B2 | 8/2011 | Taylor | |
| 8,308,670 B2 * | 11/2012 | Sandifer | ............. A61F 5/026 |
| | | | 224/263 |
| 8,556,840 B2 | 10/2013 | Burke et al. | |
| 8,708,940 B2 | 4/2014 | Jenkins, III | |
| 8,795,213 B2 | 8/2014 | Mills | |
| 8,795,215 B2 * | 8/2014 | Rossi | ............. A61F 5/026 |
| | | | 602/19 |
| 2011/0098617 A1 | 4/2011 | Ferguson et al. | |
| 2012/0078149 A1 * | 3/2012 | Azimzadeh | ............. A61F 5/024 |
| | | | 602/19 |
| 2013/0131560 A1 | 5/2013 | Ferguson et al. | |
| 2013/0131567 A1 | 5/2013 | Hinshon et al. | |
| 2013/0245522 A1 | 9/2013 | Modglin | |
| 2013/0330205 A1 | 12/2013 | Apostolides et al. | |
| 2014/0058307 A1 | 2/2014 | Marshall | |
| 2014/0100501 A1 | 4/2014 | Burke et al. | |
| 2014/0221893 A1 * | 8/2014 | Modglin | ............. A61F 5/026 |
| | | | 602/19 |
| 2016/0038331 A1 * | 2/2016 | Petterson | ............. A61B 5/1116 |
| | | | 602/19 |

OTHER PUBLICATIONS

Kim, S.D et al., "Postural Instability in Patients with Parkinson's Disease" Epidemiology, Pathophysiology and Management, CNS Drugs, 2013, 97-112, vol. 27, Springer International Publishing Switzerland 2012.

Wood, B. H. et al., "Incidence and Prediction of Falls in Parkinson's Disease: A Prospective Multidisciplinary Study" J. Neurol Neurosurg Psychiatry, 2002, 721-725, vol. 72, www.jnnp.com 2002.

de Seze, MP. et al., "An Orthosis and Physiotherapy Programme for Camptocormia: A Prospective Case Study", J. Rehabil Med, 2008, 761-765, vol. 40, Foundation of Rehabilitation Information, 2008.

International Search Report and Written Opinion for PCT US2015/048032 filed Nov. 25, 2015.

* cited by examiner

PHYSIOTHERAPEUTIC, AMBULATORY, AND MOBILITY VEST

CROSS-REFERENCE TO RELATED APPLICATIONS

This patent application claims the benefit of U.S. Provisional Patent Application No. 62/049,671 filed on Sep. 12, 2014, which is hereby incorporated by reference in its entirety.

BACKGROUND OF THE INVENTION

Field of the Invention

The present disclosure relates generally to a physiotherapeutic device, and in particular to a vest to assist individuals having ambulatory and other mobility disabilities.

Background of the Related Art

Persons with Parkinson's disease and other neurodegenerative diseases often experience issues with muscle rigidity, as well as problems with their posture and balance. At later stages of Parkinson's disease 90% of patients suffer from postural instability, and many would benefit from a device that would assist them with proper support and posture, especially during daily activities.

One form of providing support and maintaining proper posture is through a brace or a vest, such as a gait vest. Some existing back braces consist of an elongated triangular configuration for the spine system, along with adjustable shoulder straps mounted onto a lightweight waist support to allegedly assist with posture by providing a compressive force to the wearer's lower waist area. Other existing brace devices use a waist cord that can be pulled about the wearer's waist to adjust tensioning of the wearer's upper back and shoulders. Some braces provide straightening forces in the mid-torso section rather than at the shoulder.

While these prior art devices provide a means to force an individual to exhibit proper posture, none provide support and proper force vector tensioning to assist a user to maintain balance and posture while performing daily activities and functions. Moreover, prior art devices fail to offer a system allowing proper range of motion due to the rigidity and awkwardness of the devices. Furthermore, such devices provide crude and unsophisticated means of correcting posture that may even cause additional harm.

BRIEF SUMMARY OF THE INVENTION

A physiotherapeutic device has a waist tensioning system and a spine support system that may enable correction and/or maintaining of postural stance for individuals suffering from poor posture and/or neurodegenerative disease.

The device is a garment that includes a waist tensioner mechanism and a spine support system. While the device is described and depicted as a vest, one skilled in the art will appreciate, with the benefit of the present disclosure, that the device may be configured for use as any type of garment. This may include, but is not limited to, a shirt, jacket, jumpsuit, or other clothing article.

The vest includes a back portion and two front panels, wherein the back portion has a cervical expansion portion and a lumbar extension portion. The vest may include a plurality of segment panels, each exhibiting an elasticity so as to provide support and therapeutic effect. A support member pouch may be disposed on the back portion, which is configured to retain a support member in alignment with a user's spine when donning the vest. Included on a bottom portion of the vest may be a central fastener, which is configured to retain the support member within the support member pouch by covering and concealing an opening leading into the support member pouch.

A tensioner mechanism, including a central member may extend from the cervical expansion portion, where an anchor is in mechanical connection therewith. Waist straps attached to the lumbar expansion portion may be configured to be routed through the anchor and wrapped around the vest when the user dons the device. The vest also includes shoulder straps, each having a first end attached to a top, rear portion of the vest and a second end attached to the central member.

The vest may include fasteners disposed on a surface of each front panel, wherein the fasteners are configured to engage with each other so as to facilitate donning the vest and securing the vest to one's body. The vest may comprise a material that includes elastane, and the shoulder straps may comprise an elastic material. Some embodiments include an adjustment mechanism for each shoulder strap to enable shoulder strap length adjustment.

With the support member being rigid, or at least semi-rigid, the device may be configured so that when donned by the user and the waist straps are pulled, the support member applies pressure to the user's sacrum while the tension applied to the shoulder strap is adjusted. In such a configuration, the device provides a posture support and retention system during episodes of postural instability to enable individuals to maintain posture and balance while performing functions. The shoulder straps extending from the tensioning system enable generation of force vectors in a direction opposite of those that may be generated by traditional shoulder straps. The rigid support member is disposed in the vest to run parallel with the spinal column, and the shoulder straps and waist straps tie into an anchor located on a portion of the vest directly over the support member. The components, all connected together, work in concert to actively and passively adjust tension and apply pressure to straighten shoulders and improve posture and upper back support.

While these potential advantages are made possible by technical solutions offered herein, achieving them is not required. The presently disclosed device can be implemented to achieve technical advantages, whether or not these potential advantages, individually or in combinations, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages and possible applications of the present invention will be more apparent from the following more particular description thereof, presented in conjunction with the following drawings, in which.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
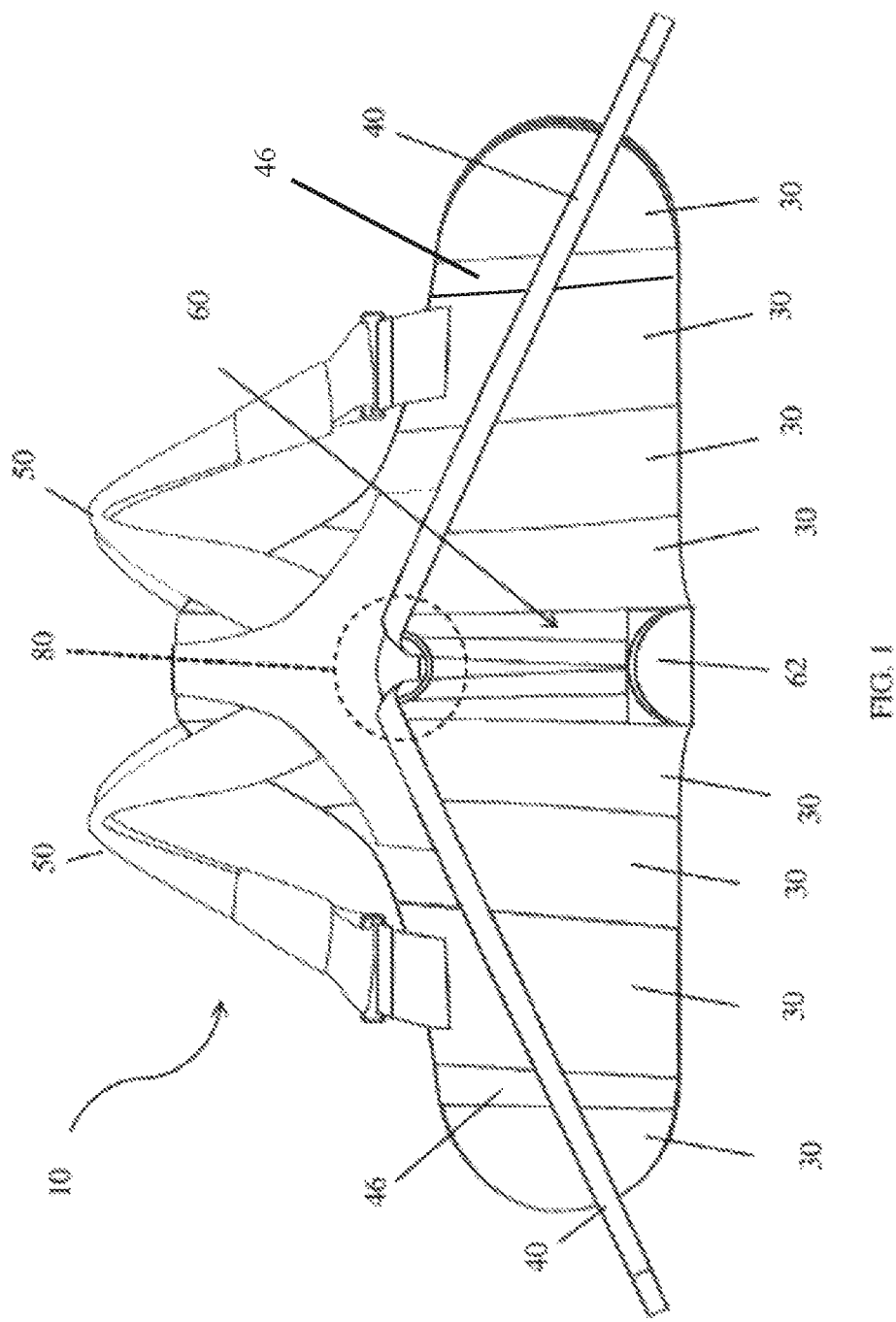
FIG. 1 illustrates an external view of the device, in accordance with an embodiment disclosed herein.
Figure 2:
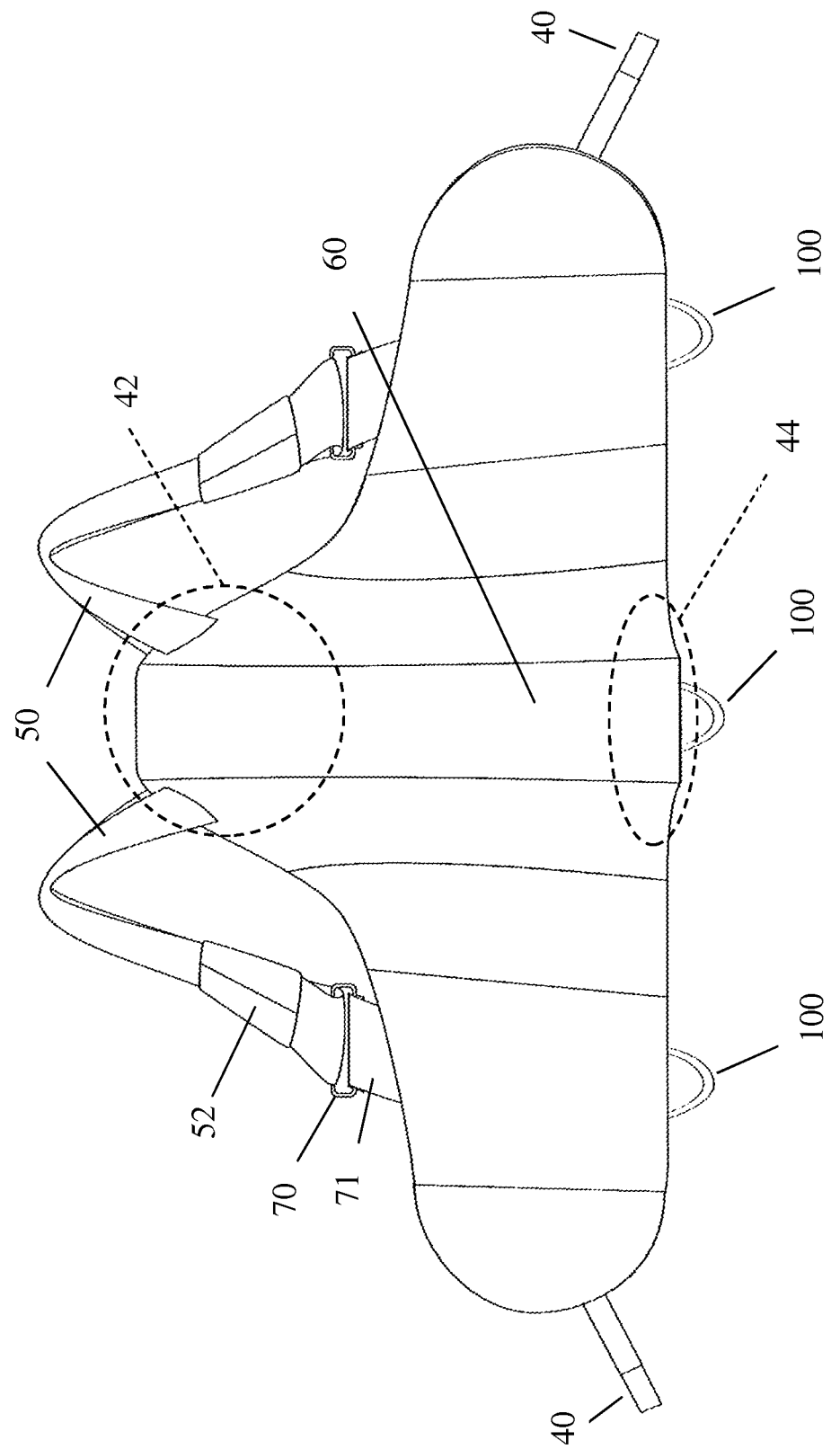
FIG. 2 illustrates an internal view of the device, in accordance with an embodiment disclosed herein.
Figure 3:
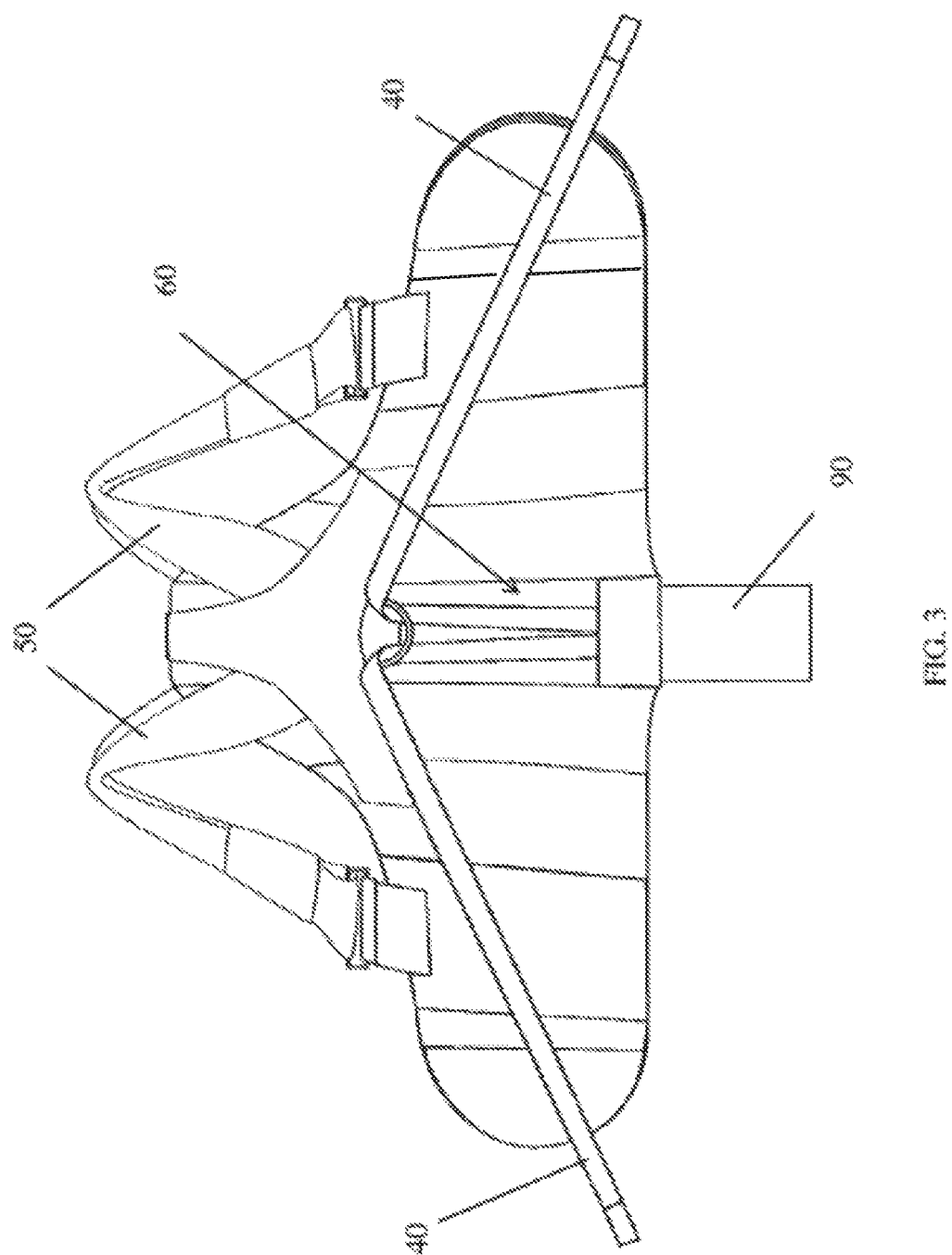
FIG. 3 illustrates another external view with the support member exposed, in accordance with an embodiment disclosed herein.

Referring now to FIGS. 1 and 2, external and internal views of the device 10 are disclosed.

The device 10 may include a vest 20 segmented into a plurality of segment panels 30 with waist straps 40, shoulder straps 50, a support member 90, and a tensioner mechanism 80. A waist tensioning system of the vest 20 may include the waist straps 40, shoulder straps 50, and tensioner mechanism 80. A spine support system of the vest 20 may include the support member 90 and plurality of segment panels 30. As disclosed herein, the waist tensioning system and the spine support system may operate in concert to enable correction and/or maintaining postural stance for individuals suffering from poor posture and/or neurodegenerative disease.

The vest 20, waist straps 40, and shoulder straps 50 may be fabricated from tough, lightweight, textile material such as nylon, cotton, canvas, elastane (i.e., Spandex® brand elastane), etc. Extending around a person's torso, or any portion thereof, when worn, the vest 20 may include an elongated fabric structure with a back portion and two front panels. The back portion has an approximate polygonal shape conjoined with a front panel at each side. The back portion may be configured to rest against a person's back while the front panels may rest against a person's chest and stomach. In such a configuration the vest 20 wraps around a person, substantially enveloping his/her torso. (See FIGS. 6 and 7).

FIG. 1 illustrates the vest 20 in a spread-open, flat position. It can be seen that the vest 20 may widen towards a back portion while becoming narrower towards the two front panels. As seen best in FIG. 2, the middle of the back portion may extend up towards a person's neck, forming a cervical extension portion 42, more so than extending down towards a person's buttock, forming a lumbar extension portion 44. This may be done to provide maximum support and comfort to a user. Generally, a person's posterior torso would require more support, whereas a person's anterior torso would require more mobility and dexterity. Thus, the back portion may be positioned at the posterior torso, whereas the front panels may be configured to connect to each other at a person's anterior torso. This connection may be achieved via fasteners 46, such as hook and pull type fasteners, disposed on surfaces of each front panel configured to engage each other to facilitate a proper and conforming fit of the vest 20 when donned by a user. This configuration may ensure that the vest 20 is comfortably secured onto the wearer, while permitting breathability and enabling the wearer to have a normal range-of-motion. Other types of fasteners for the front panels may include, but are not limited to, snaps, buckles, zippers, etc. It is understood that other configurations may be utilized as well, such as a narrowing towards the back portion, widening at a front panel, or even having the narrowest portion at a user's midsection or waistline.

The back portion, front panels, cervical expansion portion, and lumbar expansion portion may be generated form a unitary piece of fabric. Alternatively, each portion may be a separate section that is sewn together or even reversibly attached to each other via a zipper, hook-and-pull type fastener, etc.

The segment panels 30 may be integral to the vest 20 or may be removable and interchangeable sections of the vest 20. Each segment panel 30 may be defined by a change in elasticity, stiffness, and/or rigidity. While the drawings depict a different elasticity for each adjacent segment panel 30, one skilled in the art, with the benefit of the present disclosure, will appreciate that all segment panels 30 may exhibit the same elasticity, all may exhibit a different elasticity, or any combination thereof. The segment panels 30 are shown to have a length that is longer than the width; however, the width may be longer than the length, or any other combination of width-to-length ratios may be utilized. Furthermore, some segment panels 30 may exhibit elasticity in one direction while another may exhibit elasticity in a different direction. In one embodiment, the elasticity of each segment panel 30 is the width direction.

One embodiment may include some segment panels 30 that are elastic and some that are not. For example, a vest 20 may include four segment panels 30 either side of the support member pouch 60, wherein the two outer most segment panels 30 on either side are not elastic and the two inner most segment panels 30 on either side are elastic. This configuration may be done to provide maximum support and therapeutic effect. The two inner most segment panels 30 lie against the user's torso more directly that those of the two outer most segment panels 30. Consequently, therapeutic effects may be more effectively realized by having the configuration described above. One skilled in the art will appreciate, with the benefit of the present disclosure, that other combinations of elastic and non-elastic segment panels 30 may be utilized.

The widths of the segment panels 30 may be based on how much stretch is desired for compression of the individual's body to provide circumferential pressure for therapeutic effect. This may be calculated using the elastic properties of the braces materials. The widths of the segment panels 30 may also be based upon desired stretch for sizing purposes. The length of the segment panels 30 may be based of the anatomical positioning of the segment panels 30 on the vest 20. Each segment panel 30 rests along the user's body and there height is determined based on where pressure should be applied to the user to obtain therapeutic effect.

This may be done to accommodate persons of various weights, waist size, height, and/or whether the vest is being worn overtop or underneath clothing. A segmented panel 30 configuration may also provide desired levels of support, pressure, and dexterity at certain points of a person's torso. For example, although a person may require less support in the anterior torso, she may still require support so segment panels 30 in the abdominal region may be more rigid. While therapeutic effects of the vest 20 via the segment panels 30 are normally achieved by the panels 30 working in conjunction with the other components of the vest 20, a desired physiotherapeutic effect may be achieved by applying pressure at an oblique section via a segment panel 30.

Other therapeutic effects may be realized from the various configurations of the segment panels 20. For example, different combinations of elastic and non-elastic segment panels 30, as well as varying degrees of elasticity, may be utilized to modify comfort levels, balancing, and posture.

At least one waist strap 40 may be provided with the vest 20, which may be attached to a portion of the support member pouch 60 via a first end of the waist strap 40, whereas the second end of the waste strap 40 is free. The free end may be configured to extend vertically up through the tensioner mechanism 80. The strap 40 may then loop around a user's waist to be connected to the vest 20, or to another free end of a second waist strap 40, to not be connected at all, or not even wrapped around the waist of the user. (See FIGS. 6 and 7). The waist strap 40 may enable application of the tensioning system by a user. For example, pulling the waist strap 50 adjusts tension applied to shoulder straps 50 and the support member 90 so that pressure is applied to the sacrum of the wearer, and stability and support are provided for the shoulders and entire torso. Details of the tensioning and spine support systems of the vest 20, and how they generate proper force vectors to assist with posture and other therapeutic functions will be discussed later.

The first end of the waist strap 40 may be permanently affixed to the vest 20 via stitching. Alternatively, it may be reversibly secured via a central fastener 62. The central fastener 62 may include a hook and pull type securement, and may also be configured to retain the support member 90 within the support member pouch 60 by covering and concealing an opening leading into the support member pouch 60. For example, both ends of the waist strap 40 may be provided with complementary hook and pull type fasteners, and the support member pouch 60 and the central fastener 62 may be provided with additional complementary hook and pull type fasteners. Furthermore, the central fastener 62 may be configured as a flap that is permanently affixed to a bottom portion of the vest 20. An end of the waist strap 40 may be secured to the central fastener 62 and the opposite end may be routed up through the tensioner mechanism 80, as described earlier. Concurrently, the support member 90 may be placed within the support member pouch 60 and secured in place with the central fastener 62, thereby providing proper and adequate securement for both the waist straps 40 and the support member 90.

Figure 6:
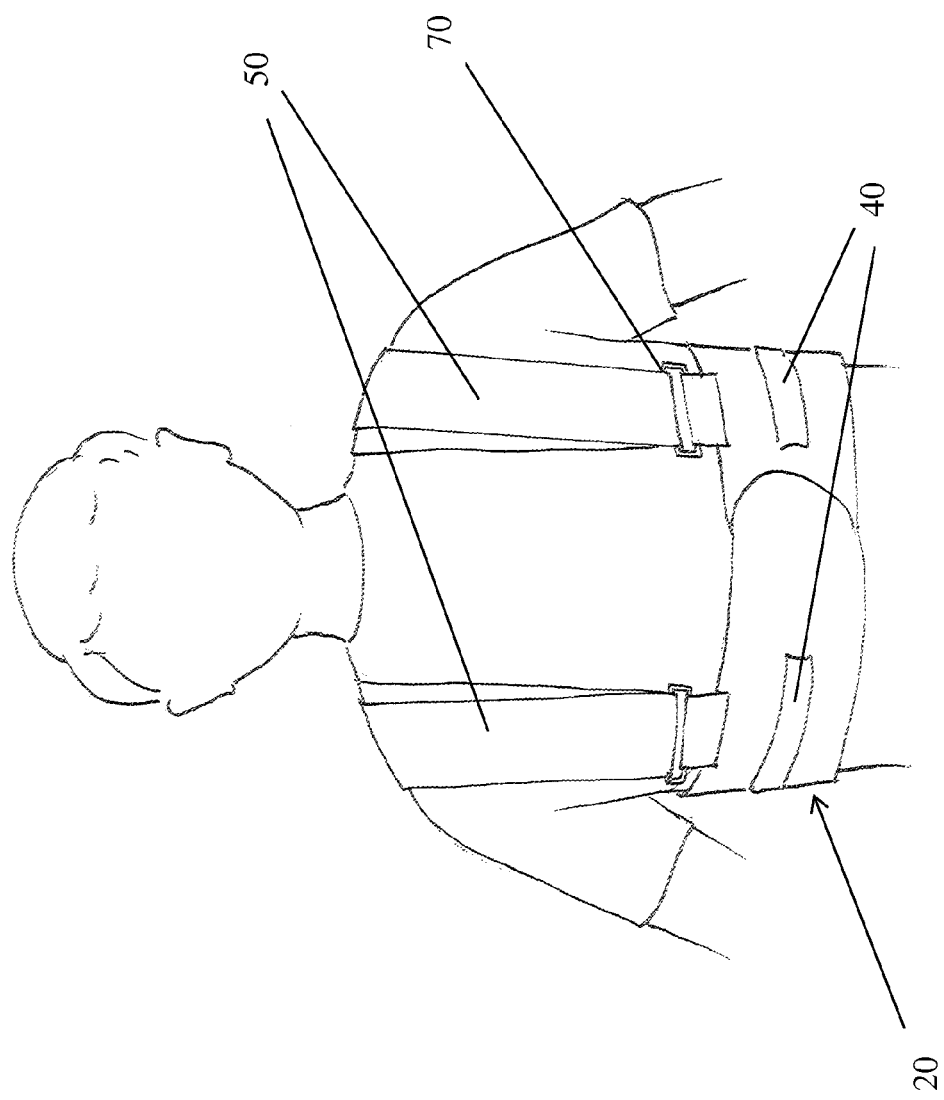
FIG. 6 is an environmental front view of a user donning the device.
Figure 7:
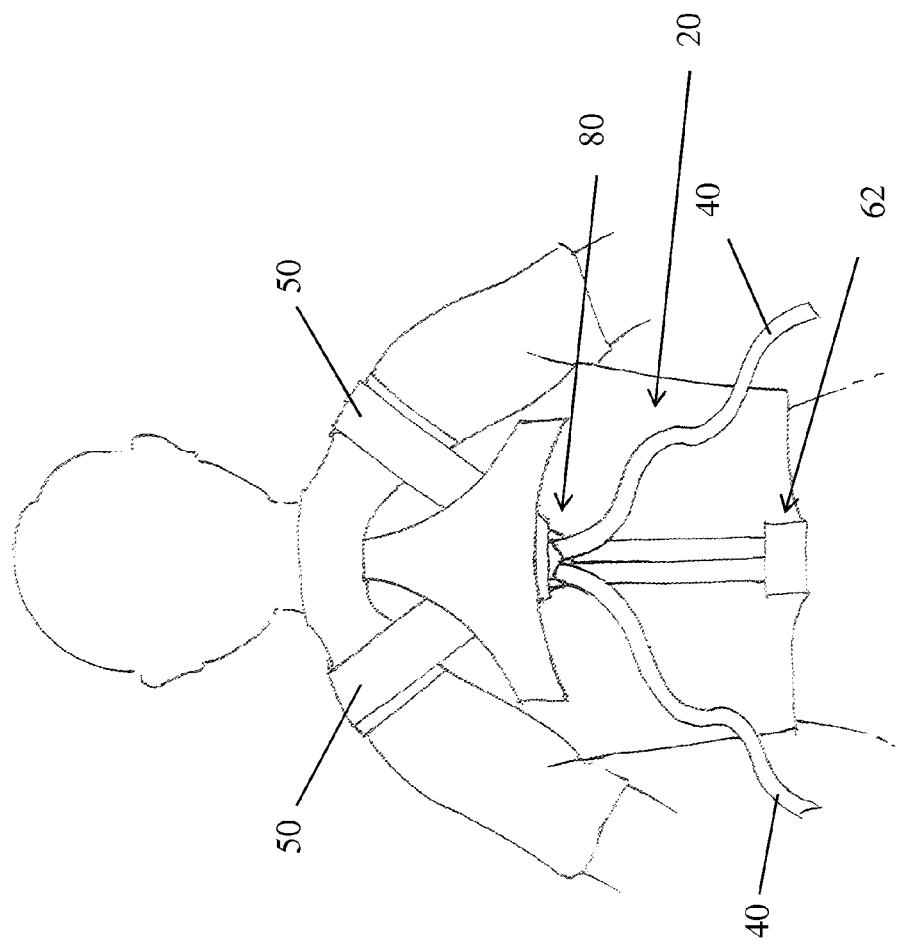
FIG. 7 is an environmental rear view of a user donning the device.

The free ends of the waist straps 40 may also include a fastener to enable a user to wrap and/or "stow" the waist straps 40 when not in use by wrapping the straps 40 around the vest 20 and securing the straps 40 to each other or to another complementary fastener located on the vest 20, as shown in FIG. 6.

Figure 4:
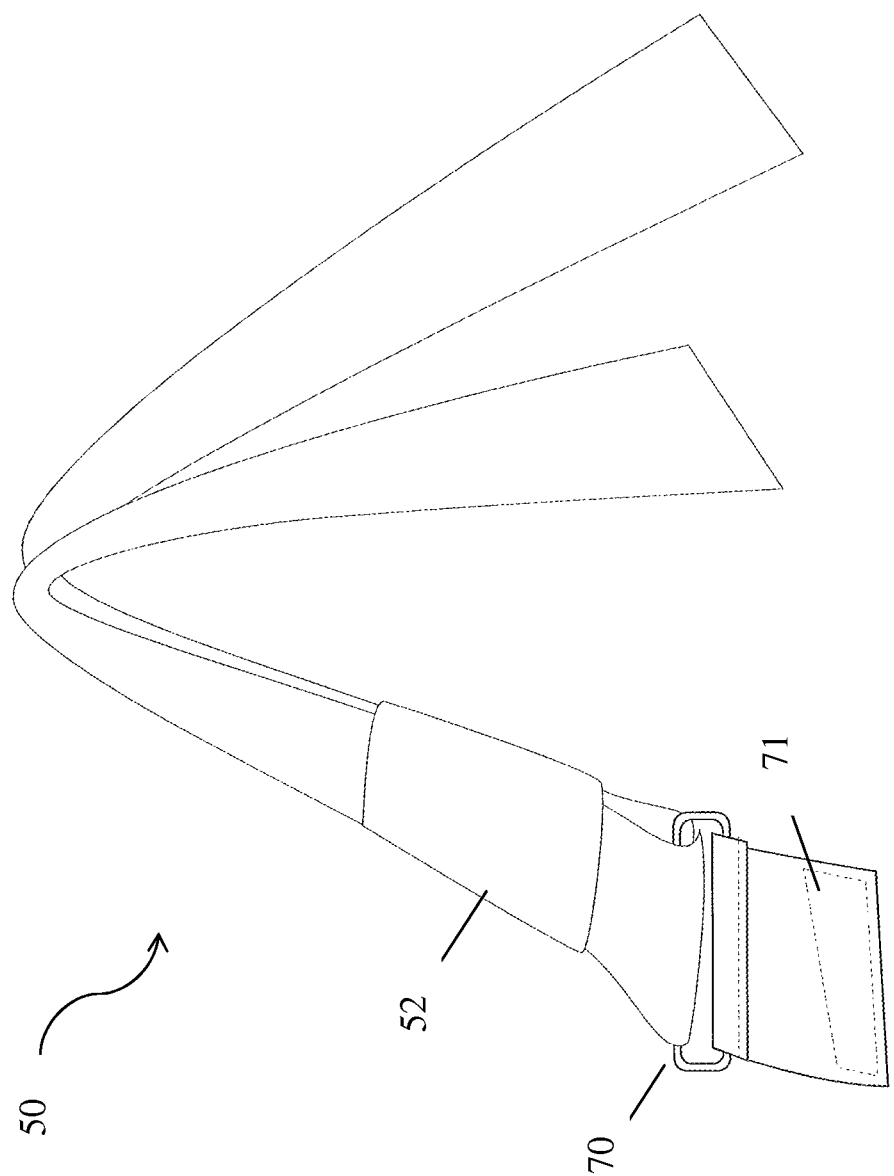
FIG. 4 illustrates a side view of the shoulder straps of the device, with the vest portion omitted for ease of illustration, in accordance with an embodiment disclosed herein.
Figure 5:
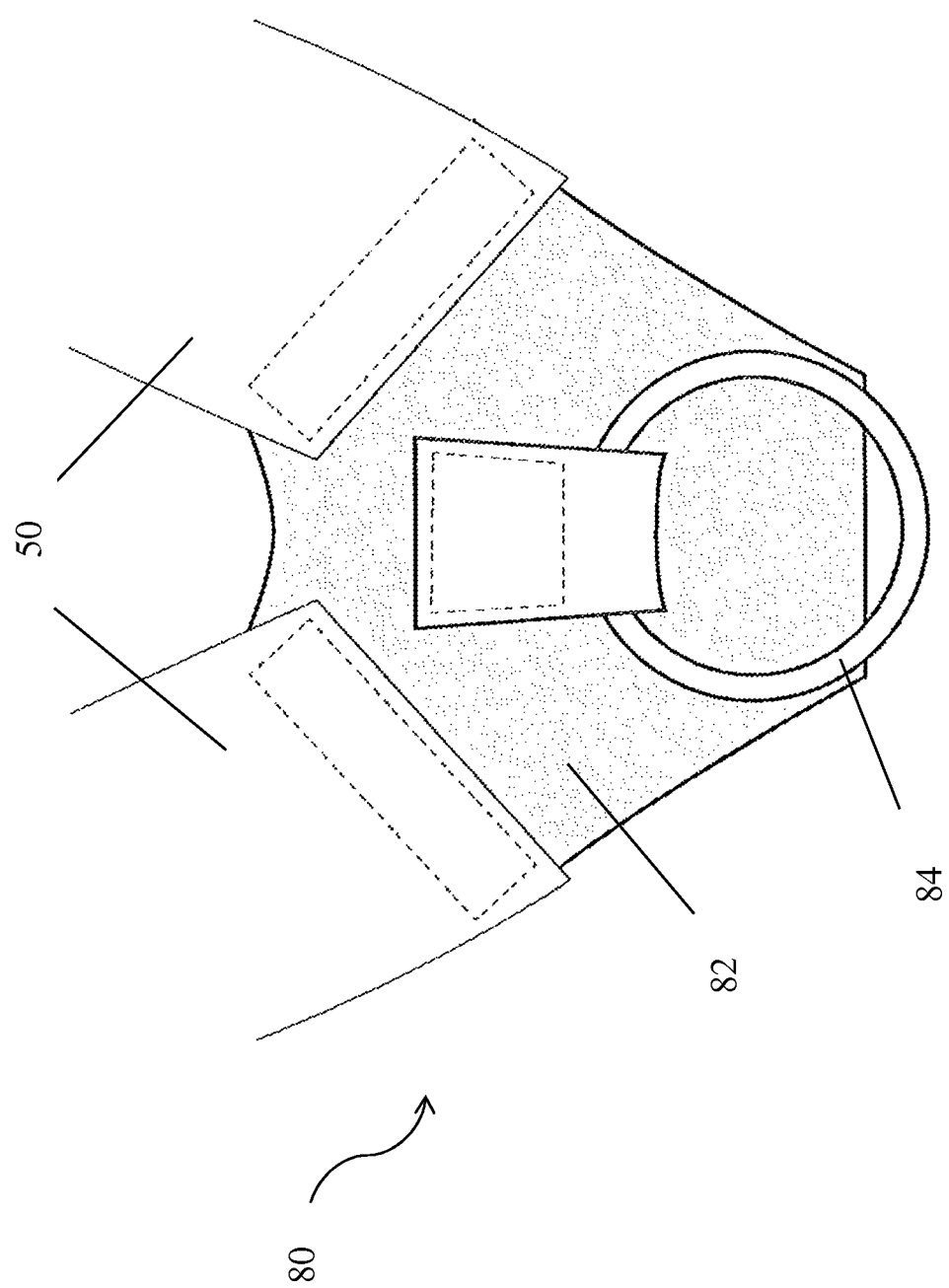
FIG. 5 illustrates an exploded partial view of the tensioner mechanism, in accordance with an embodiment disclosed herein.

The device 10 may include at least one shoulder strap 50 extending from a top, rear portion of the vest 20, and may be attached via stitching at a first end, whereas the second end may be attached to a central member 82 of the tensioner mechanism 80 (See FIG. 4). An adjustment mechanism 70, for example, a buckle, may be provided to adjust the length of each strap 50. A shoulder pad 52 may be included with the shoulder strap 50 to provide added support and comfort for a user, which may include a sleeve with padding disposed on a surface thereof. The shoulder pads 52 may also keep portions of the shoulder straps 50 aligned, thus making it easier to don the device. Any portion of the shoulder strap 50 may be elastic to assist with directing and balancing force vectors and to provide a desired therapeutic effect and/or comfort. For example, the first end may be connected to the vest via elastic extenders 71. (See FIG. 5). Each shoulder strap 50 may be constructed of a single, elastic member so as to exhibit a consistent stretch. Each shoulder strap 50 may exhibit the same elasticity as the other shoulder strap 50, further providing consistent support for a user employing the device 10. Changing the width of each strap 50 may be done to modify the amount of force applied to move the shoulders back into the correct therapeutic position.

The vest 20 may be provided with a support member pouch 60 that is substantially in alignment with a user's spine when the vest 20 is donned. The support member pouch 60 may be configured to receive and retain a support member 90. At last one support member 90 may be inserted into the support member pouch 60 by sliding it therethrough, and it may be held in place by the central fastener 62 in a similar manner described above. Alternatively, the support member 90 may be reversibly inserted via sliding through an opening at a top of the support member pouch 60, wherein the bottom of the support member pouch 62 may be sealed. Alternatively, or in addition, any number of support members 90 may be permanently secured within the support member pouch 60 via other methods, such as stitching. Furthermore, a first support member 90 may be permanently secured within the support member pouch 60 via stitching while other support members 60 may be reversibly secured via the central fastener 62.

In addition, any support member 90 may be integral to the vest 20. For example, the vest may include a central panel 30 that has the stiffness and rigidity to serve as the support member 90. Removing the support member 90 at the discretion of a user may be beneficial to facilitate cleaning and maintenance of the device 10.

The support member 90 is a rigid and/or semi-rigid structure, such as a plate for example, which may be fabricated from aluminum, steel, plastic, composite fiber, etc. After the vest 20 has been donned and secured against a user's body, the support member 90 places pressure against the sacrum to serve as a fulcrum for bearing the load being applied at the shoulder straps 50 as a user performs functions such as walking, sitting, standing, moving, etc. The support member 90 may have dimensions of 3¼-6¼ inches wide and 16-24 inches high. The width may be based upon the location of the paraspinal muscles. The support member 90 preferably span the width of the gap between these muscles to create the therapeutic effect desired without painful pressure on the spine. The height may be based on the height of the individual specified for each size of the brace. While the support member 90, combined with the straps 50 and main band of the vest 20, provide therapeutic effect, the full correction of posture may best be achieved once the individual has tensioned the straps 50 using the waist straps 40 to force the shoulders back and into the correct position.

A tensioner mechanism 80 may be disposed on a rear portion of the vest 20, which may be provided with a central member 82 in mechanical connection with an anchor 84, such as a D-ring, an O-ring, a buckle, a pulley, shackle, etc. that may facilitate routing at least one waist strap 40 and enable sliding of the waist strap 40 so as to adjust tensioning of the tensioning system. Pulling on the waist strap 40 acts upon the central member 82, whereby it transfers force in a controlled manner to lift the shoulders via the shoulder straps 50 and ensures that the support member 90 is in proper position to act upon the sacrum.

As described earlier, the segment panel 30, waist straps 40, shoulder straps 50, tensioner mechanism 80, and support member 90 all act in concert to generate a postural correcting system that enables complete support of the spine, shoulders, and waist. For example, a second end of each shoulder strap 50 meets the tensioner mechanism 80 posteriorly along a cervical extension portion 42 to provide complete, balanced upper back support to the wearer. This configuration ensures that pulling on the waist straps 40 results in pulling the shoulder's back, which in conjunction with the other features of the device 10, provides the complete, balanced upper back support. This intersection is attached to the waist tensioning system via the anchor 84 that may move vertically, due to the central member 82, across a thoracic region of the vest 20 when subjected to variations in force vectors. A user may use the waist straps 40 to easily apply force in an ergonomic horizontal direction, which is transmitted into a vertical force via the tensioner mechanism 80 to act upon the shoulder straps 50 and support member 90, thereby providing the wearer with the proper postural-correcting forces for their upper back and shoulders. Thus, pulling on the waist straps 40 enables a user to supply the desired level of posture support, while the other features of the vest 20 continue to provide therapeutic effects.

The segment panels 30 provide additional support and therapeutic pressure at certain portions of the body. The pressure provided by the device 10 is a circumferential pressure around the trunk of the user. This may relieve pressure in the lower back and may help push the user against the support member 90.

Once comfortably secured to a user's body, a single active motion (e.g., pulling the waist straps) of the waist straps 40 may provide support and therapeutic effects from multiple components of the device 10. Components, such as the support member 90 and segment panel 30, provide passive posture and therapeutic support without actuation of the waist straps 40. These components may provide passive support in addition to providing active support. The ease of use and effectiveness of the device 10 renders the vest 20 well suited for users suffering from neurodegenerative type disease.

In an alternative embodiment, a system of cross-straps positioned at both the front of the vest 20 and the back of the vest 20 may be provided. Actuating the waist straps 40 would automatically provide the shoulders of the wearer with enough tension to maintain an upright position. This would enable proper support and posturing with an actuation of a single waist strap 40, whereas actuation of both waist straps may be required to generate the same effect without the cross-strap configuration. This adds convenience for a user because activation of the tensioning system to affect the entire back may be achieved by actuation of a single waist strap 40.

In an alternative embodiment, a shoelace corset system installed within the vest 20 may be used to increase the support provided by the device 10. The shoelace corset system operates via a drawstring and cord lock mechanism. The cord lock mechanism is configured to reversibly secure the drawstring at a desired position when drawn through the lock mechanism. The drawstring may be connected to a lace-network that when acted upon circumferentially withdrawals the vest 20, or at least portions thereof, to generate a conforming fit to a user's body.

In an alternative embodiment, the vest 20 includes at least one belt loop 100 located at a bottom rear portion of the vest 20 and that is configured to reversibly attach to trousers of a user. (See FIG. 2). Tensioning system straps may be provided at the front of the vest 20 and configured to be pulled downward by the user. Upon pulling the tensioning straps, the central member 82 is acted upon, as described above, to generate the force vectors necessary to correct and/or maintain posture while the spine system provides postural support.

In an alternative embodiment, a multi-gear system which may include a winch, may be included with the vest to assist with providing and/or maintaining proper tensioning and postural support. The winch may be located within the vest 20. The winch may be used to set a desired level of tension and support by selectively drawing/releasing/locking tensioning cables. A cable network extends from the winch and may be attached to various portions of the vest 20, including the tensioning mechanism 80. The winch may be mechanical or electro-mechanical. The winch may be easily accessible from the front of the vest 20, and it may be operable by hand or remote control. Some embodiments may include a simple two-gear system.

In an alternative embodiment, portions of the vest 20 may include inflatable sections and/or bladders that may be inflatable via fluid, such as water, air, etc. The inflatable sections may be configured to reversibly and/or permanently retain bladders. In either case, the bladder includes a valve suitable for selectively inflating and deflating the bladder at the discretion of the user. In a situation where the bladder is permanently retained within the inflatable section, a valve stem may be provided that extends through the vest 20. By inflating certain sections and to certain pressures, tension and support can be more easily tailored to accommodate the condition that a user is immediately encountering.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A posture support device, comprising:
   a garment including a back portion conjoined with two front panels, wherein a middle of the back portion extends upward to form a cervical extension portion and extends downward to form a lumbar extension portion;
   a support member pouch disposed on the back portion configured to retain a support member in alignment with a user's spine;
   a tensioner mechanism, including a central member extending from the cervical extension portion and an anchor in mechanical connection with the central member;
   at least one waist strap attached to the lumbar extension portion and configured to be routed through the anchor and wrapped around the garment; and,
   at least one shoulder strap having a first end attached to a top, rear portion of the garment and a second end attached to the central member.

2. The posture support device recited in claim 1, further comprising fasteners disposed on a surface of each front panel, wherein the fasteners are configured to enable engagement with each other.

3. The posture support device recited in claim 1, wherein the garment comprises a material that includes elastane.

4. The posture support device recited in claim 1, wherein the at least one shoulder strap comprises a material that is elastic.

5. The posture support device recited in claim 1, wherein the at least one shoulder strap includes an adjustment mechanism.

6. The posture support device recited in claim 1, wherein when the at least one waist strap is pulled, the support member applies pressure to the user's sacrum while tension-adjustment is applied to the at least one shoulder strap via the tensioner mechanism.

7. A posture support device, comprising:
 a garment including a back portion conjoined with two front panels, wherein a middle of the back portion extends upward to form a cervical extension portion and extends downward to form a lumbar extension portion;
 a support member pouch disposed on the back portion configured to retain a support member in alignment with a user's spine;
 a tensioner mechanism, including a central member extending from the cervical extension portion and an anchor in mechanical connection with the central member;
 at least one waist strap attached to the lumbar extension portion and configured to be routed through the anchor and wrapped around the garment; and,
 at least one shoulder strap having a first end attached to a top, rear portion of the garment and a second end attached to the central member;
 wherein the garment includes a plurality of segment panels, wherein at least one segment panel exhibits elasticity different from another segment panel.

8. The posture support device recited in claim 7, further comprising fasteners disposed on a surface of each front panel, wherein the fasteners are configured to enable engagement with each other.

9. The posture support device recited in claim 7, wherein the garment comprises a material that includes elastane.

10. The posture support device recited in claim 7, wherein the at least one shoulder strap comprises a material that is elastic.

11. The posture support device recited in claim 7, wherein the at least one shoulder strap includes an adjustment mechanism.

12. The posture support device recited in claim 7, wherein when the at least one waist strap is pulled, the support member applies pressure to the user's sacrum while tension-adjustment is applied to the at least one shoulder strap via the tensioner mechanism.

13. A posture support device, comprising:
 a garment including a back portion conjoined with two front panels, wherein a middle of the back portion extends upward to form a cervical extension portion and extends downward to form a lumbar extension portion;
 a support member pouch disposed on the back portion configured to retain a support member in alignment with a user's spine;
 a central fastener disposed at a bottom portion of the garment;
 a tensioner mechanism, including a central member extending from the cervical extension portion and an anchor in mechanical connection with the central member;
 at least one waist strap attached to the lumbar extension portion and configured to be routed through the anchor and wrapped around the garment; and,
 at least one shoulder strap having a first end attached to a top, rear portion of the garment and a second end attached to the central member;
 wherein the garment includes a plurality of segment panels; and,
 wherein the central fastener is configured to retain the support member within the support member pouch by covering and concealing an opening leading into the support member pouch.

14. The posture support device recited in claim 13, further comprising fasteners disposed on a surface of each front panel, wherein the fasteners are configured to enable engagement with each other.

15. The posture support device recited in claim 13, wherein the garment comprises a material that includes elastane.

16. The posture support device recited in claim 13, wherein the at least one shoulder strap comprises a material that is elastic.

17. The posture support device recited in claim 13, wherein the at least one shoulder strap includes an adjustment mechanism.

18. The posture support device recited in claim 13, wherein when the at least one waist strap is pulled, the support member applies pressure to the user's sacrum while tension-adjustment is applied to the at least one shoulder strap via the tensioner mechanism.

19. The posture support device recited in claim 13, wherein the support member is rigid.

20. The posture support device recited in claim 13, wherein the device is configured so that when donned by the user and the at least one waist strap is pulled, the support member applies pressure to the user's sacrum and tension applied to the at least one shoulder strap is adjusted.

* * * * *